(12) United States Patent
Ude

(10) Patent No.: US 6,406,004 B1
(45) Date of Patent: Jun. 18, 2002

(54) METHOD FOR IMPARTING A CERTAIN ODOR IMPRESSION TO A PERSON AND APPARATUS FOR PERFORMING THE METHOD

(75) Inventor: Christiane Ude, Seeheim-Jugenheim (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/589,776

(22) Filed: Jun. 8, 2000

(30) Foreign Application Priority Data

Jun. 11, 1999 (DE) .......................................... 199 26 795
Jul. 9, 1999 (DE) .......................................... 199 32 107

(51) Int. Cl.⁷ .................................................. B01F 3/04
(52) U.S. Cl. .......................... 261/26; 261/30; 261/104; 261/DIG. 88; 261/DIG. 89; 422/124
(58) Field of Search ................... 261/26, 104, DIG. 88, 261/DIG. 89, 30; 422/124

(56) References Cited

U.S. PATENT DOCUMENTS

| | | | | |
|---|---|---|---|---|
| 3,628,829 A | * | 12/1971 | Heilig .......................... | 352/85 |
| 4,835,879 A | * | 6/1989 | Egelstad ........................ | 34/97 |
| 5,610,674 A | * | 3/1997 | Martin .......................... | 352/85 |
| 5,949,522 A | * | 9/1999 | Manne .......................... | 261/26 |

FOREIGN PATENT DOCUMENTS

DE        38 43 871 A1        6/1990

* cited by examiner

*Primary Examiner*—Robert A. Hopkins
(74) *Attorney, Agent, or Firm*—Michael J. Striker

(57) ABSTRACT

The method for imparting a certain odor impression to a person (2) by means of a perfume preparation includes passing an air stream (5) over and/or through a perfume preparation (3) to form a perfumed air stream (6) and directing the perfumed air stream (6) at least approximately to a region (7) from which air is drawn in through the nose (8) of the person (2). The apparatus for providing a certain odor impression to a person (2) includes a device (4) for producing at least one air stream (5), a device for holding a perfume preparation (3) in the at least one air stream (5) so that the at least one air stream passes over and/or through the perfume preparation, whereby at least one perfumed air stream (6) is formed, and a device for directing the at least one perfumed air stream (6) at least approximately toward a region (7) from which air is drawn in through the nose (8) of the person (2).

17 Claims, 4 Drawing Sheets

METHOD FOR IMPARTING A CERTAIN ODOR IMPRESSION TO A PERSON AND APPARATUS FOR PERFORMING THE METHOD

BACKGROUND OF THE INVENTION

1. Field of the Invention

The present invention relates to a method of imparting a predetermined odor impression to a person by means of a perfume preparation. It also relates to an apparatus for imparting a certain odor impression to a person by means of a perfume preparation.

2. Prior Art

Current methods of making an olfactory impression attempt to fill an entire @ room with perfume. This has the consequence that a change in the type of odor is scarcely possible since a concentration of perfume is present in the room and because of that concentration unpleasant mixed odors would be produced. Thus it is not possible to provide an individual person with a pleasant olfactory sensation, without also exposing other persons in the room to this odor. Indeed DE 38 43 871 describes a method for providing a predetermined odor impression for only one individual person, which has the disadvantage that a perfume preparation is arranged in the nose region of the person by means of a clip.

SUMMARY OF THE INVENTION

It is an object of the present invention to provide a method of imparting a predetermined odor impression to an individual of the above-described kind that does not have the above-described disadvantage.

It is another object of the present invention to provide an apparatus for imparting a predetermined odor impression to an individual of the above-described kind that does not have the above-described disadvantage.

The method according to the invention for providing a certain odor impression to a person includes passing an air stream over and/or through a perfume preparation to form a perfumed air stream and directing the perfumed air stream at least approximately to a region from which air is drawn in through the nose of the person.

In a preferred embodiment of the method the air stream is at least approximately at room temperature. Because of this preferred feature a change in the odor impression due to heating the perfumed air stream is prevented.

The apparatus according to the invention for providing a certain odor impression to a person comprises
  means for producing at least one air stream;
  means for holding a perfume preparation in the at least one air stream to form at least one perfumed air stream; and
  means for directing the at least one perfumed air stream at least approximately toward a region from which air is drawn through the nose of the person.

The means for producing the at least one air stream preferably comprises at least one electric blower. The air stream is produced and directed in a simple manner because of this preferred feature.

In a preferred embodiment of the invention the apparatus comprises a single compact unit including the means for producing an air stream and the means for holding the perfume preparation in the air stream to form a perfumed air stream. The means for producing the air stream in this embodiment advantageously includes an air intake, a rotatable impeller or fan with a drive means and an airflow straightener for forming the airflow produced by the rotating impeller or fan to make the air stream.

The apparatus for providing a certain odor impression to a person also is connected with a unit for treating the hair on the scalp.

The compact unit of the preferred embodiment is also advantageously provided with a holder for the perfume preparation that is formed so that the air stream passes through and/or around the perfume preparation.

The perfume preparation advantageously is formed as a card (economical punched part), which provides simple handling and cost advantages.

In another preferred embodiment the perfume preparation comprises an absorptive material. A largely uniform dispensing of the perfume contained in the perfume preparation is possible because of a capillary effect in the absorptive material.

A card comprising an absorptive material, insertable according to choice, provides a very economical perfume preparation in which perfume is absorbed at least by a part of the absorptive material. When the card is provided with a perfume protecting sheath or jacket, the perfume in the perfume preparation can be advantageously conserved for later use.

In a preferred embodiment in which the absorptive material of the perfume preparation is cylindrical, the absorptive material may be covered with a sheathing jacket or cap. This provides a suitable means of testing the perfume for its odor.

An arbitrary selection of individual odor impressions is possible by means of a system with different types of perfume.

In a preferred embodiment the perfume preparation is combined with its holder or holding means to form a disposable part, in order to provide freedom from germ contamination.

The cards used as the perfume preparation are provided with information regarding the type of perfume contained in them, for example by means of at least one colored area or region, at least one symbol and/or a written description.

In another preferred embodiment the apparatus is provided with an air stream forming attachment for preparation of the air stream so that because of a fine swirling and braking of the air flow ideal conditions for detecting an odor by the nose are present and a very small concentration of perfume is sufficient. Because of the very small perfume concentration no substantial inhalation of the perfume occurs, but the threshold for stimulating the olfactory organ is exceeded.

Alternatively the air stream can be produced by compressed air or vapor or steam instead of a blower.

The apparatus can be controlled by means of a programmed controller according to various requirements, for example according to the parameters time, airflow intensity and choice of odor impression.

The apparatus can also be provided with means for regulating the airflow forming the air stream in a preferred embodiment. For example, the blower may be provided with a rotation speed-adjusting device to control the airflow.

In another preferred embodiment of the invention the perfume preparation may be combined with a perfume container so that it is unnecessary to replace a spent perfume preparation.

The perfume preparation may advantageously also be formed as an absorptive airflow diffuser and/or airflow forming attachment.

The invention provides the following advantages:

The perfume is activated and released cold at room temperature, not by heat (and because of that the olfactory impression is not changed by heat).

The perfume is released by a natural evaporation from alcohol in a reproducible amount and performs as desired.

The perfume is metered in a controlled manner to the nose so that field of view of the person exposed is not limited or so that the skin is not irritated by contact with the perfume.

The air breathed by the person is charged with the perfume so that the person can move freely and also breath freely, i.e. the person need not breath through an air filter or the like. No overdosing of the perfume occurs during a deep breath because of individual adjustment of the perfume concentration.

Because the lowest concentration of the perfume is guided to the person to be exposed to the perfume no odor impressions or the like are conveyed to other persons in the same room as the person to be exposed, i.e. the effect is exclusively limited to the targeted person, in order to avoid an effect on others.

In a preferred embodiment with a swirl screen the airflow is formed so that because of a fine swirling and braking of the air flow ideal conditions for detecting an odor by the nose are present and a very small concentration of perfume is sufficient. Because of the very small perfume concentration no substantial inhalation of the perfume occurs, but the threshold for stimulating the olfactory organ is exceeded.

The perfume provided to the vicinity of the nose can be arbitrarily turned on and off, so that a desensitization of the sense of smell can be prevented.

The type of perfume is arbitrarily changeable without resulting in mixed odors as a side effect.

The apparatus can be provided as an attachment or as an ancillary device in a hair treatment unit used in a hair styling salon.

The odor impression is provided with the help of an airflow, preferably produced with a fan.

Alternatively the odor impression can be provided by producing the airflow with means that are different from the fan, namely with pressurized air or vapor, as long as the airflow can be controlled and directed.

To start the action of the perfume the fan is turned on or a cover is removed from it.

It is particularly preferably when the fan does not draw the air used to form the air flow from the treatment room (of the hair salon) possibly containing other odor-producing substances, but from outside of the room.

Swirling of the air does not take place during a permanent wave treatment in which the customer receiving the permanent wave treatment is being provided with an odor impression by the method according to the invention. Air from the permanent wave treatment possibly containing unpleasant odors therefore does not reach the region from which air is drawn in through the nose. The volatilization of the permanent wave treatment composition does not effect the odor impression, especially when heat is used at the same time as the permanent wave treatment.

Because of the perfumed air stream directed into the region from which air enters the nose the pleasant odor impression dominates, when extremely volatile substances with a clearly unpleasant odor escape from the head or when cosmetic preparations with an unpleasant odor are applied to the hair.

The air stream from the fan can also be controlled or switched off during the acting time, which can occur by covering the air stream or by switching off or controlling the fan itself. The regulation of the air stream from the fan can take place automatically or directly by action of the customer.

A suitable regulation can take place under control of a device integrated in the apparatus according to the invention or in a programmable controller in the apparatus. The method according to the invention can begin automatically under program control when the treatment unit is started, by means of a start button on the apparatus or by insertion of the apparatus according to the invention on the treatment unit.

The fan is dimensioned and arranged so that the perfumed air stream reaching the region from which air is drawn into the nose of the customer is sufficient to provide that region with perfume, but so that perfume is not provided to the surrounding area.

The fan is positioned or an air stream forming attachment is provided so that the eyes of the customer are not irritated by the air stream. The air stream is thus guided, for example, so that it is inclined forward over the customer into the region from which air is drawn in through the nose, also at the level or the mouth or chin of the customer. The air motion and the flow direction are thus adjusted so that the eyes of the treated person are not irritated, since the swirling action required for breathing in the perfumed air does not directly contact the face of the customer.

There are different ways to guide the airflow so that an air stream can be directed or oriented so that it can provide a pleasant cooling air motion around the customer during a heat treatment of the head. However no draft is formed as in a simple fan operation because of the definitely slowed air stream speed. The heated air outside of the conical airflow from the fan is entrained with it and moved accordingly without forming an unpleasant cooling airflow directly on the face.

In other embodiments a flow is provided which is just diffuse enough so that the perfume reaches the region in front of the nose in sufficient concentration, but does not produce the impression of a draft. For especially draft-sensitive persons the air drawn in by the fan can be heated somewhat. However the heating should not be so great that a negative change occurs in the impression produced by the perfume.

A rotation speed adjustment for the fan or blower is provided for the customer so that the intensity of the perfume impression and the strength of the airflow can be individually adjusted. In an additional embodiment the intensity can also be adjusted by a reduction of the airflow outlet opening or by artful packing of the diffuser.

In a further embodiment two fans or blowers are arranged side-by-side or laterally. These two fans or blowers conduct air enriched with perfume material into the vicinity of the chin and nose, so that a perfumed air stream is formed and directed so that no irritation of the ears and eyes occurs.

The perfume comprises a volatile material, preferably diluted with alcohol.

The perfume preparation comprises a perfume-containing reservoir, which supplies perfume from its interior to the outside for the entire treatment time by capillary action in a preferred embodiment.

The perfume preparation is preferably not in direct contact with the fan or the radiating and diffuser component, so that they are not attacked by possibly reactive perfumes.

The perfume preparation is preferably formed as a consumable, i.e. disposable, part. A new fresh perfume preparation is used for each individual perfume treatment, so that the perfume preparation is germ-free during each treatment.

In other embodiments the perfume preparation can comprise an absorptive material (fleece) and can be connected with a reservoir, which can provide a dose of the perfume that is absorbed by the fleece. A closure device is provided for the reservoir, since a permanent moistening of the absorptive material would lead to a perfuming of the entire room in which the treatments are occurring over a certain time period.

The perfume reservoir comprises strip, e.g. a viscose fleece, soaked with the perfume, attached to a support, which is introduced into the air stream leaving the means for producing the air stream and fixed in it.

In other embodiments the air flow-diffuser is formed so that it is absorptive and wet with the perfume and acts as both perfume reservoir and diffuser. The material can be both absorptive and also porous so that the perfume can be deposited in sufficient amounts in the pores.

Examples of the use of the method and apparatus according to the invention as include a method of improving mood of an individual by providing a pleasant odor impression;

a method of improving the experience of an individual or customer during waiting or treatment time, e.g. in hair styling; and a method of replacing or overcoming the unpleasant odor of a hair treatment composition during heating during the acting time of the hair treatment composition with the pleasant aroma or odor of the perfume. For the latter application an optimum direction or orientation of the airflow is required, so that the rising fumes from the cosmetics are not swirled by the perfume stream and reach the nose region. Areas of use include, e.g., permanent wave treatments, hair dyeing, air tinting, hair drying and action of care compositions.

BRIEF DESCRIPTION OF THE DRAWING

The objects, features and advantages of the invention will now be illustrated in more detail with the aid of the following description of the preferred embodiments, with reference to the accompanying figures in which.

DESCRIPTION OF THE PREFERRED EMBODIMENTS

Figure 1:
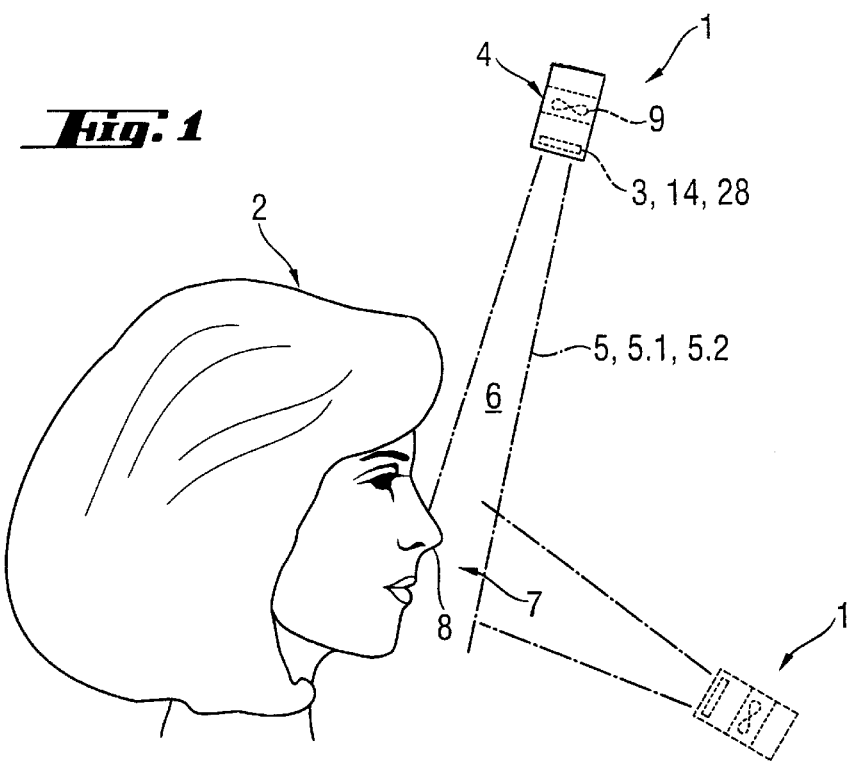
FIG. 1 is a diagrammatic side view of an apparatus according to the invention for imparting a certain odor impression to a person.

FIG. 1 shows one embodiment of an apparatus according to the invention for imparting an odor impression to a person by means of a perfume preparation 3. The apparatus 1 is provided with a means 4 for producing at least one air stream 5, in which the perfume preparation is arranged so that the air stream 5 passes around and through it. A perfumed air stream 6 is formed from the air stream 5 by means of the perfume preparation 3 and is directed at least approximately to a region 7 from which air is drawn into the nose 8 of the person 2. The apparatus 1 can be arbitrarily positioned at any angular position according to the requirements by means of suitable positioning means and can be combined arbitrarily with the unit 12, in order to provide a pleasant perfume experience. Because of the method and apparatus according to the invention also (unpleasant) outside odors can be eliminated or masked, if necessary. The device or means 4 for producing at least one air stream 5 comprises at least one electric blower with a rotatably driven impeller or fan 9 in the embodiment shown in the drawing. The means for producing the air stream however in other unshown embodiments can include an unshown pressurized air tank containing pressured air which is used to form an air stream 5.1 or an unshown source of vapor or steam.

Figures 2, 3:
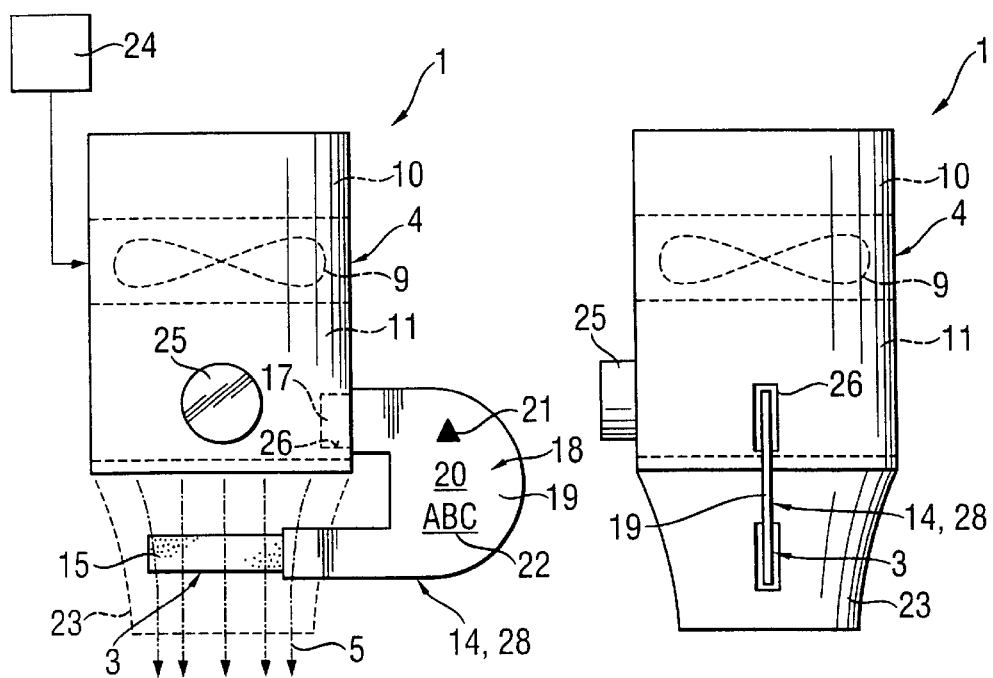
FIG. 2 is a side view of a first embodiment of an apparatus according to the invention for imparting a certain odor impression to a person with a first perfume preparation, but without its air stream forming attachment.
FIG. 3 is a different side view of the apparatus of FIG. 2 with its air stream forming attachment.

FIGS. 2 and 3 show apparatus 1 in greater detail. An air intake 10 and the at least one electric blower with the rotatably driven impeller or fan 9 are arranged at one end of the apparatus. An airflow straightener 11 is arranged at the other end of the apparatus 1 downstream of the electric blower. The air stream 5 issuing from the airflow straightener 11 passes over and through the perfume preparation 3, which is held on a card 14.

The perfume preparation 3 is placed on a holder 19. The holder 19 is provided with a plug connector 17, which is inserted in a receptacle 26 in the apparatus 1, in order to connect it to the apparatus 1. The surface of the holder 19 is provided with information 18 regarding the type of perfume in the perfume preparation 3, for example by means of a certain colored area or region 20, a predetermined symbol 21 and/or a printed description 22. The air stream 5 is directed by means of a nozzle-shaped air stream forming attachment 23 on the apparatus 1, which has been shown with dashed lines in FIG. 2. The nozzleshaped air stream forming attachment 23 directs and prepares the perfumed air stream 6 so that because of a fine swirling and braking of the airflow ideal conditions for detecting an odor by the nose are present, so that a very small concentration of perfume is sufficient. Because of that no inhalation of perfume occurs, but the threshold for odor detection is immediately exceeded. The device 4 for producing the at least one air stream 5 can be controlled according to the requirements of the application by means of a schematically shown programmable controller 24, for example with the parameters time, airflow intensity and for change of type of perfume by change of perfume preparation. The airflow 5 may be individually adjusted by adjusting means 25 for adjusting the rotation speed of the electric blower with the rotatable impeller or fan 9.

Figure 4:
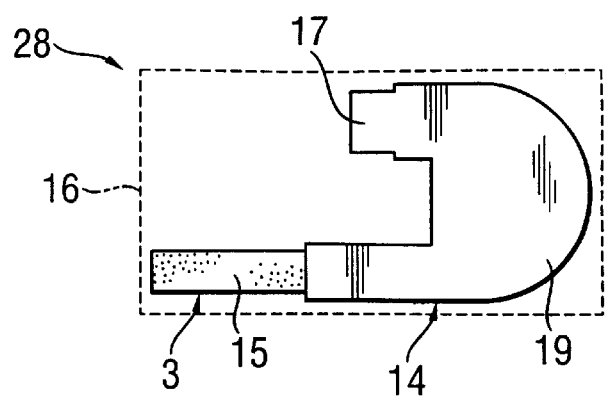
FIG. 4 is a side view of a first holder for a perfume preparation.

FIG. 4 shows the perfume preparation 3 placed on a card 14 and is provided together as a disposable part 28 with a perfume protecting jacket 16, which is removed before use of the perfume preparation 3.

Figure 5:
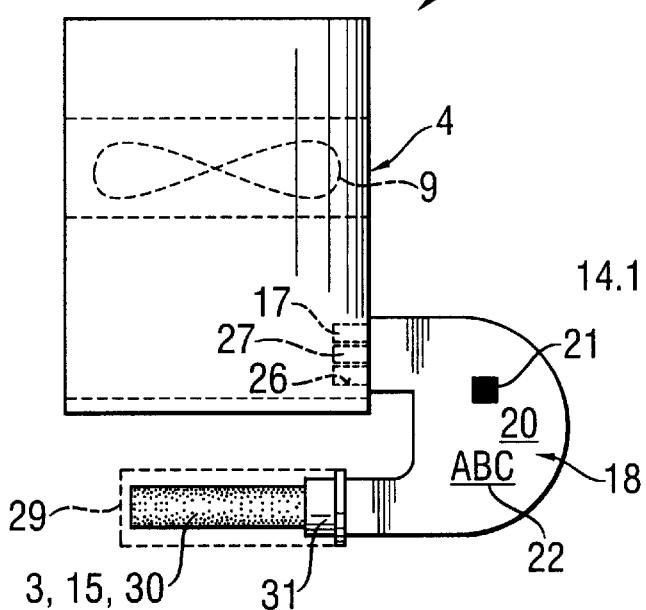
FIG. 5 is a side view of an apparatus according to the invention with a second holder for a perfume preparation.
Figure 6:
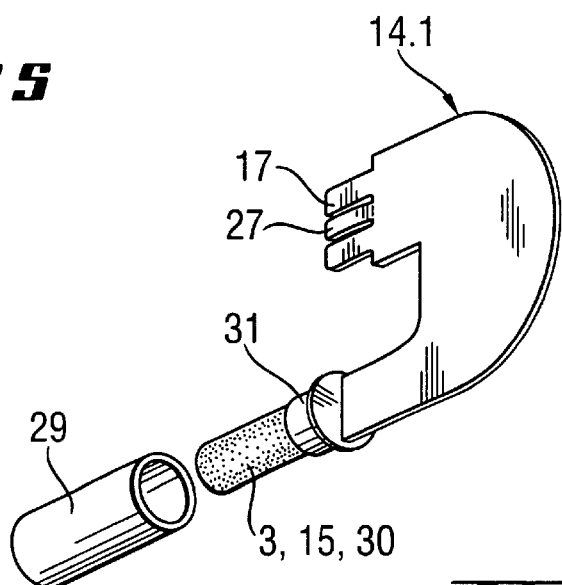
FIG. 6 is a perspective view of the second holder for a perfume preparation.

In FIG. 5 the apparatus 1 has a cylindrical perfume preparation support 30, which is covered with a sheathing jacket or cap 29 prior to use and because of that can also be taken off for a short time to test the scent. In order to provide a secure but releasable connection of the plug connector 17 in the receptacle 26 the plug it connector 17 is provided with a resilient tongue (FIG. 6), which itself is located in the receptacle so that it is again releasable. The card 14.1 is made from plastic material in one piece with the plug connector 17 and a receiving part 31 for the cylindrical perfume preparation 30.

Figure 7:
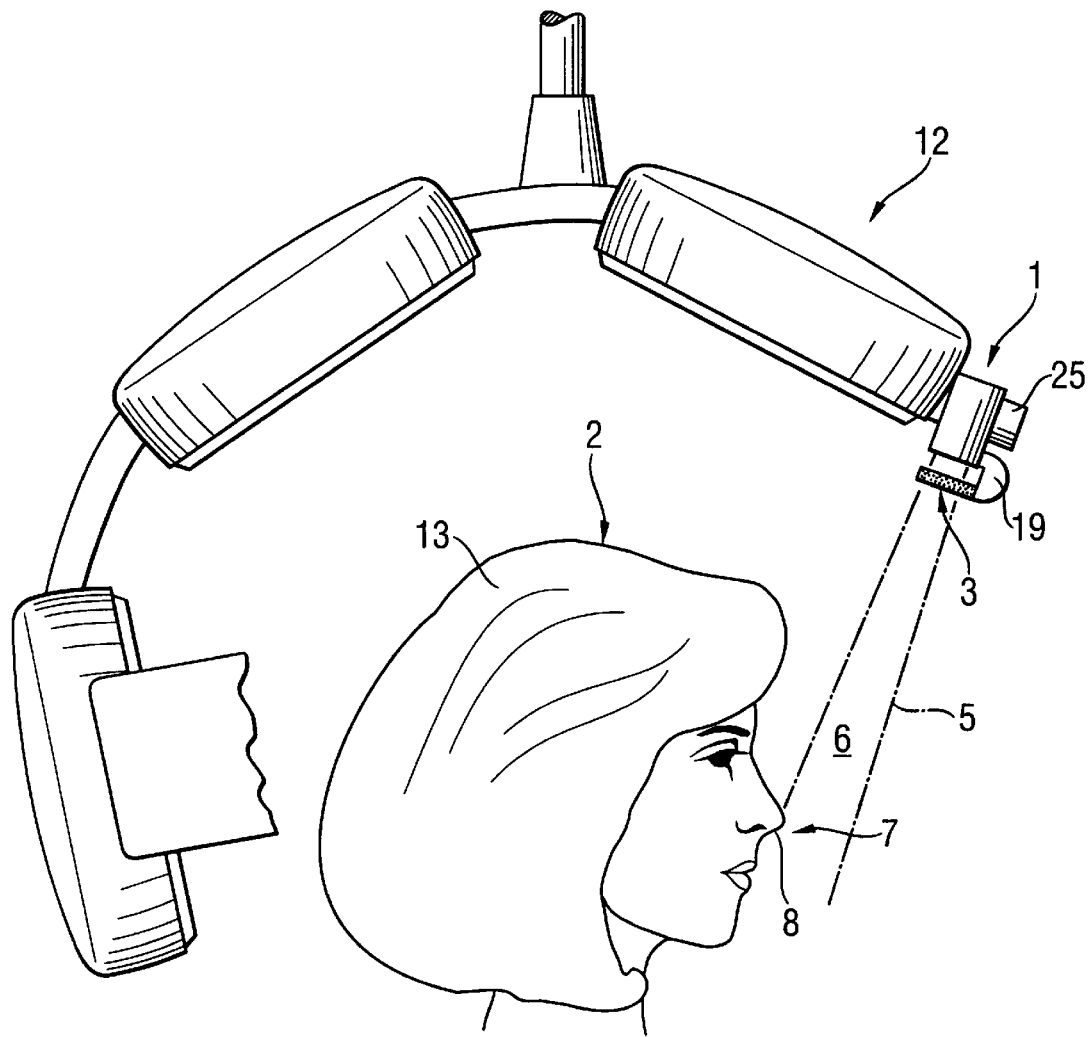
FIG. 7 is a side view of an apparatus according to the invention for imparting a certain odor impression to a person in use with a hair treatment unit.
Figure 8:
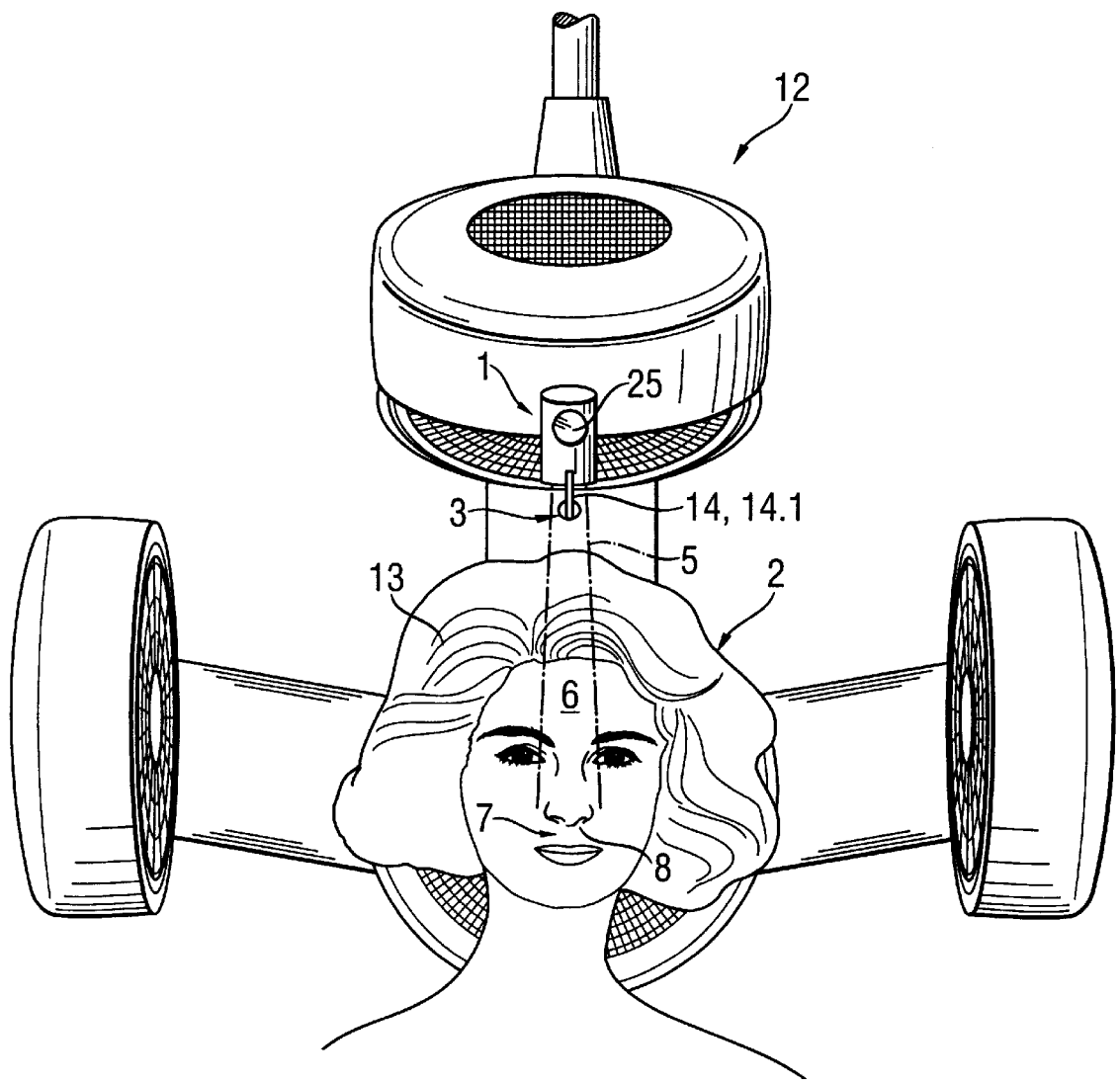
FIG. 8 is a front view of the hair treatment unit and apparatus according to the invention shown in FIG. 7.

The apparatus 1 according to the invention is shown in FIGS. 7 and 8 with, for example, a heat-treating unit 12 for scalp hair, as marketed by the assignee under the trade name "Climazon Millenium".

The disclosures in German Patent Applications 199 26 795.2 and 199 32 107.8 of Jun. 11, 1999 and Jul. 9, 1999 respectively are incorporated here by reference. These German Patent Applications describe at least a part of the invention described hereinabove and claimed in the claims appended hereinbelow and provide the basis for a claim of priority for the instant invention under 35 U.S.C. 119.

While the invention has been illustrated and described as embodied in a method and apparatus of imparting a predetermined odor impression to a person by means of a perfume preparation, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art fairly constitute essential characteristics of the generic or specific aspects of this invention.

What is claimed is new and is set forth in the following appended claims.

I claim:

1. An apparatus (1) for providing a certain odor impression to a person (2) comprising:
   means (4) for producing at least one air stream (5);
   means for holding a perfume preparation (3) in the at least one air stream (5) so that the at least one air stream passes over and/or through the perfume preparation, whereby at least one perfumed air stream (6) is formed;
   means for directing the at least one perfumed air stream (6) at least approximately toward a region (7) from which air is drawn in through the nose (8) of the person (2); and
   means for connection with a hair treatment unit (12) for treating scalp hair.

2. The apparatus as defined in claim 1, wherein the means (4) for producing the at least one air stream comprises at least one electric blower with a rotatably driven impeller or fan (9).

3. The apparatus as defined in claim 2, further comprising means for regulating at least one airflow forming the at least one air stream.

4. The apparatus as defined in claim 3, wherein said means for regulating the at least one airflow comprises a rotation speed controller for controlling a rotation speed of the at least one electric blower.

5. The apparatus as defined in claim 1, further comprising a compact unit and wherein said compact unit includes said means (4) for producing the at least one air stream and said means for holding the perfume preparation, and wherein said means for producing the at least one air stream comprises an air intake (10), a rotatable impeller or fan (9) and a airflow straightener (11) for forming an airflow produced by the rotatable impeller or fan.

6. The apparatus as defined in claim 1, wherein said means (4) for producing said at least one air stream comprises a source of pressurized air (5.1) or vapor or steam (5.2).

7. The apparatus as defined in claim 1, further comprising a programmable controller (24) for controlling said means (4) for producing said at least one air stream.

8. An apparatus (1) for providing a certain odor impression to a person (2) comprising:
   means (4) for producing at least one air stream (5);
   means for holding a perfume preparation (3) in the at least one air stream (5) so that the at least one air stream passes over and/or through the perfume preparation, whereby at least one perfumed air stream (6) is formed, wherein said means for holding the perfume preparation (3) is formed by a card (14); and
   means for directing the at least one perfumed air stream (6) at least approximately toward a region (7) from which air is drawn in through the nose (8) of the person (2).

9. The apparatus as defined in claim 8, further comprising a disposable part (28) comprising said perfume preparation and said means for holding the perfume preparation (3).

10. The apparatus as defined in claim 8, further comprising a perfume supply container and wherein a perfume material is supplied continually to said perfume preparation from the perfume supply container.

11. The apparatus as defined in claim 8, wherein the perfume preparation comprises an absorptive airflow diffuser.

12. An apparatus (1) for providing a certain odor impression to a person (2) comprising:
   means (4) for producing at least one air stream (5);
   means for holding a perfume preparation (3) in the at least one air stream (5) so that the at least one air stream passes over and/or through the perfume preparation, whereby at least one perfumed air stream (6) is formed, wherein said perfume preparation (3) comprises an absorptive material and wherein said absorptive material is formed as a card (14); and
   means for directing the at least one perfumed air stream (6) at least approximately toward a region (7) from which air is drawn in through the nose (8) of the person (2).

13. An apparatus (1) for providing a certain odor impression to a person (2) comprising:
   means (4) for producing at least one air stream (5);
   means for holding a perfume preparation (3) in the at least one air stream (5) so that the at least one air stream passes over and/or through the perfume preparation, whereby at least one perfumed air stream (6) is formed, wherein said, means for holding the perfume preparation (3) is formed by a card (14) and wherein said card is provided with a perfume-protecting jacket (16); and
   means for directing the at least one perfumed air stream (6) at least approximately toward a region (7) from which air is drawn in through the nose (8) of the person (2).

14. An apparatus (1) for providing a certain odor impression to a person (2) comprising:

means (4) for producing at least one air stream (5);

means for holding a perfume preparation (3) in the at least one air stream (5) so that the at least one air stream passes over and/or through the perfume preparation, whereby at least one perfumed air stream (6) is formed, wherein said perfume preparation comprises a cylindrical absorptive material, and wherein the means for holding the perfume preparation includes a removable sheathing cap (29) for said absorptive material; and means for directing the at least one perfumed air stream (6) at least approximately toward a region (7) from which air is drawn in through the nose (8) of the person (2).

15. An apparatus (1) for providing a certain odor impression to a person (2) comprising:

means (4) for producing at least one air stream (5);

means for holding a perfume preparation (3) in the at least one air stream (5) so that the at least one air stream passes over and/or through the perfume preparation, whereby at least one perfumed air stream (6) is formed, wherein the means for holding the perfume preparation in the at least one air stream is provided with information (18) regarding the type of perform contained in the perfume preparation (3); and means for directing the at least one perfumed air stream (6) at least approximately toward a region (7) from which air is drawn in through the nose (8) of the person (2).

16. An apparatus (1) for providing a certain odor impression to a person (2) comprising:

means (4) for producing at least one air stream (5);

means for holding a perfume preparation (3) in the at least one air stream (5) so that the at least one air stream passes over and/or through the perfume preparation, whereby at least one perfumed air stream (6) is formed, wherein the means for holding the perfume preparation in the at least one air stream is provided with information (18) regarding the type of perform contained in the perfume preparation (3) and wherein the means for holding the perfume preparation includes at least one colored region (2), at least one symbol (21) and/or at least one printed description (22), in order to provide said information (18); and means for directing the at least one perfumed air stream (6) at least approximately toward a region (7) from which air is drawn in through the nose (8) of the person (2).

17. An apparatus (1) for providing a certain odor impression to a person (2) comprising:

means (4) for producing at least one air stream (5);

means for holding a perfume preparation (3) in the at least one air stream (5) so that the at least one air stream passes over and/or through the perfume preparation, whereby at least one perfumed air stream (6) is formed; and means for directing the at least one perfumed air stream (6) at least approximately toward a region (7) from which air is drawn in through the nose (8) of the person (2), wherein said means for directing the at least one perfumed air stream (6) at least approximately toward said region (7) comprises a nozzleshaped airflow forming attachment (23).

* * * * *